US009464268B2

(12) United States Patent
Liang (10) Patent No.: US 9,464,268 B2
(45) Date of Patent: Oct. 11, 2016

(54) HARVESTING MICRO ALGAE

(71) Applicant: COLORADO SCHOOL OF MINES, Golden, CO (US)

(72) Inventor: Hongjun Liang, Arvada, CO (US)

(73) Assignee: COLORADO SCHOOL OF MINES, Golden, CO (US)

( * ) Notice: Subject to any disclaimer, the term of this patent is extended or adjusted under 35 U.S.C. 154(b) by 0 days.

(21) Appl. No.: 14/556,675

(22) Filed: Dec. 1, 2014

(65) Prior Publication Data

US 2015/0152376 A1   Jun. 4, 2015

Related U.S. Application Data

(62) Division of application No. 13/011,582, filed on Jan. 21, 2011, now abandoned.

(60) Provisional application No. 61/297,533, filed on Jan. 22, 2010.

(51) Int. Cl.

| C12N 1/12 | (2006.01) |
| C07K 14/71 | (2006.01) |
| C12N 1/02 | (2006.01) |
| C12N 13/00 | (2006.01) |
| H01F 1/00 | (2006.01) |

(52) U.S. Cl.
CPC ............... *C12N 1/12* (2013.01); *C07K 14/71* (2013.01); *C12N 1/02* (2013.01); *C12N 13/00* (2013.01); *H01F 1/0018* (2013.01)

(58) Field of Classification Search
CPC ...................................... C07K 14/71
See application file for complete search history.

(56) References Cited

U.S. PATENT DOCUMENTS

| 4,708,930 A | 11/1987 | Kortright et al. |
| 4,743,543 A | 5/1988 | Kortright |
| 4,892,935 A | 1/1990 | Yoshida et al. |
| 4,914,021 A | 4/1990 | Toth et al. |
| 4,918,164 A | 4/1990 | Hellstrom et al. |
| 4,921,789 A | 5/1990 | Salem et al. |
| 4,921,790 A | 5/1990 | O'Brien |
| 4,939,240 A | 7/1990 | Chu et al. |
| 4,963,484 A | 10/1990 | Kufe |
| 5,053,489 A | 10/1991 | Kufe |
| 5,110,911 A | 5/1992 | Samuel et al. |
| 5,270,163 A | 12/1993 | Gold et al. |
| 5,475,096 A | 12/1995 | Gold et al. |
| 5,512,443 A | 4/1996 | Schlom et al. |
| 5,693,763 A | 12/1997 | Codington et al. |
| 5,808,005 A | 9/1998 | Codington et al. |
| 5,855,866 A | 1/1999 | Thorpe et al. |
| 5,892,019 A | 4/1999 | Schlom et al. |
| 5,892,020 A | 4/1999 | Mezes et al. |
| 6,284,470 B1 * | 9/2001 | Bitner ..................... C12N 1/02 435/6.16 |

| 2005/0031692 A1 | 2/2005 | Beyerinck et al. |
| 2010/0143721 A1 | 6/2010 | Chen et al. |
| 2011/0268791 A1 | 11/2011 | Liu et al. |

FOREIGN PATENT DOCUMENTS

| WO | 9413804 | 6/1994 |
| WO | 9738134 | 10/1997 |
| WO | 9833941 A1 | 8/1998 |
| WO | 9907724 A1 | 2/1999 |
| WO | 2008152490 A2 | 12/2008 |
| WO | 2009110939 A2 | 9/2009 |

OTHER PUBLICATIONS

Galluzzi et al. J of Applied Microbiology, 2006, 101:36-43.*
del Campo et al. J of Magnetism and Magnetic Materials, 2005, 293:33-40.*
Hu et al. The Plant J., 2008, 54:621-639.*
Adlish et al., "Identification of a Putative Cell Receptor for Human Cytomegalovirus", Virology (1990), 176, 337-345.
Allen, "Ligand-Targeted Therapeutics in Anticancer Therapy", Nat. Rev. Cancer (2002), 2, 750-763.
Allen, "Long-circulating (sterically stabilized) liposomes for targeted drug delivery", Trends Pharmacol. Sci. 15:215 (Jul. 1994).
Asakura et al., "Interaction Between Particles Suspended in Solutions of Macromolecules", Journal of Polymer Science, vol. XXXIII, pp. 183-192 (1958).
Binkley et al., "RNA ligands to human nerve growth factor", Nuc. Acids Res. (1995), 23(16), 3198-3205.
Bird et al., "Single-Chain Antigen-Binding Proteins", Science (1988), 242, 423-426.
Blumen et al., "Unique Uptake of Acid-Prepared Mesoporous Spheres by Lung Epithelial and Mesothelioma Cells", Am. J. Respir. Cell Mol. Biol. 36:333 (Mar. 2007).
Bosma et al., "Ultrasound, a New Separation Technique to Harvest Microalgae", Journal of Applied Psychology, vol. 15, pp. 143-153 (2003).
Buranda, "Biomimetic Molecular Assemblies on Glass and Mesoporous Silica Microbeads for Biotechnology", Langmuir 2003, v19(5):1654-1663.
Carel et al., "Structural Requirements for C3d,g/Epstein-Barr Virus Receptor (CR2/CD21) Ligand Binding, Internalization, and Viral Infection", J. Biol. Chem. (1990), 265(21), 12293-12299.
Carnegie Mellon, "Porin Structure and Function", https:www.bio.cmu/.edu/courses/03441/TermPapers/99TermPapers/TwoCom/porin_details.html, cached Google Feb. 1, 2001.
Carter, "Potent antibody therapeutics by design", Nature Reviews Immunology (2006), 6, 343-357.
Champaloux, "Function and Structure of OmpF Porin", http://www.bio.davidson.edu/Couurses/Molbio/MolStudents/spring2005/Champaloux/first/html, cached Feb. 14, 2006 from wayback machine).

(Continued)

*Primary Examiner* — Bin Shen
(74) *Attorney, Agent, or Firm* — Dorsey & Whitney LLP (57) ABSTRACT

A reusable composite paramagnetic particle may comprise a paramagnetic core encased by a protective material to which is grafted a tendril layer comprising a plurality of polymeric chains. The polymeric chains may be designed to interact with a microorganism. The interaction between the microorganism and the polymeric chain may be electrostatic. The nanoparticle may be used in a method to isolate or recover microorganisms from solutions using an externally applied magnetic field.

20 Claims, 4 Drawing Sheets

(56) References Cited

OTHER PUBLICATIONS

Chen et al., "Potassium Permanganate as an Alternative Preoxidant for Enhancing Algal Coagulation—Pilot and Bench Scale Studies", Environmental Technology, vol. 29, pp. 721-729 (2008).
Chen et al., "Temperature-responsive magnetite/PEO-PPO-PEO block copolymer nanoparticles for controlled drug targeting delivery", Langmuir, 2007, 23:12669-12676.
Co et al., "Isolation and biochemical characterization of the mammalian reovirus type 3 cell-surface receptor", Proc. Nat'l. Acad. Sci. U.S.A (1985), 82, 1494-1498.
Denardo et al., "Development of tumor targeting bioprobes (111In-chimeric L6 monoclonal antibody nanoparticles) for alternating magnetic field cancer therapy", Clin Cancer Res. 2005, 11(19 Suppl):7087s-7092s.
Deng et al., "Monodisperse Magnetic Single-Crystal Ferrite Miscrospheres", Angew. Chem. Int. Ed. 2005, vol. 44, pp. 2782-2785.
Divakaran et al., "Flocculation of Algae Using Chitosan", Jounal of Applied Phycology, vol. 14, pp. 419-422 (2002).
Dong et al., "General Synthesis of Mesoporous Spheres of Metal Oxides and Phosphates", JACS 125:4976 (2003).
Duan et al., "Reexamining the effects of particle size and surface chemistry on the magnetic properties of iron oxide nanocrystals: new insights into spin disorder and protein relaxivity", The J of Phys. Chem., 2008, 112(8):8127-8131.
Eppstein et al., "Epidermal growth factor receptor occupancy inhibits vaccinia virus infection", Nature (1985), 318, 663-665.
Ferrari, "Cancer Nanotechnology: Opportunities and Challenges", Nature Rev. Cancer (2005), 5, 161-171.
Fu et al., "Control of Molecular Transport Through Stimuli-Responsive Ordered Mesoporous Materials", Adv. Mater. 15:1262 (Aug. 5, 2003).
Gregoriadis, "Engineering Liposomes for Drug Delivery: Progress and Problems", Trends Biotechnol. 13:527 (Dec. 1995).
Han et al., "Generalized Fluorocarbon-Surfactant-mediated Synthesis of Nanoparticles with Various Mesoporous Structures", Angew. Chem. Int. Ed. 44:288 (2005).
Hanisch et al., "Structural Studies on Oncofetal Carbohydrate Antigens (CA 19-9, CA 50, and CA 125) Carried by O-Linked Sialyloligosaccharides on Human Amniotic Mucins", Carbohydr. Res. (1988), 178, 29-47.
Harlow et al., "Using Antibodies: A Laboratory Manual", Cold Spring Harbor, New York, Cold Spring Harbor Laboratory Press, 1999, 5 pages.
Hinoda et al., "Immunochemical Characterization of Adenocarcinoma-Associated Antigen YH206", Int'l Cancer Journal (1988), 42, 653-658.
Hoffman et al., "Silica-Based Mesoporous Organic-Inorganic Hybrid Materials", Angew. Chem. Int. Ed. 45:3216 (2006).
Holliger et al., "Diabodies: Small bivalent and bispecific antibody fragments", Proc. Natl. Acad. Sci. USA (1993) 90, 6444-6448.
Holliger et al., "Engineered antibody fragments and the rise of single domains: Antibody engineering and manufacture", Nature Biotech (2005), 23(9), 1126-1136.
Holzinger et al., "Preparation of Amorphous Metal-Oxide-Core Polymer-Shell Nanoparticles via a Microemulsion-Based Sol-Gel Approach", Chem. Mater., vol. 15, pp. 4944-4948 (2003).
Hu et al., "Cytosolic Delivery of Membrane-Impermeable Molecules in Dendritic Cells Using pH-Responsive Core-Shell Nanoparticles", Nano Lett. 7:3056 (2007).
Hu et al., "Microalgal Triacylglycerols as Feedstocks for Biofuel Production: Perspectives and Advances", The Plant Journal, vol. 54, pp. 621-639 (2008).
Huston et al., "Protein engineering of antibody binding sites: Recovery of specific activity in an anti-digoxin single-chain Fv analogue produced in *Escherichia coli*", Proc. Natl. Acad. Sci. U.S.A. (1988), 85, 5879-5883.
Ishida et al., "Related Glycoprotiens from Normal Secretory and Malignant Brest Cells: Purification and Initial Comparative Characterizations", Tumor Biol. (1989), 10, 12-22.
Jain, "The Next Frontier of Molecular Medicine: Delivery of Therapeutics", Nat. Med. 4:544 (1998).
Jellinek et al., "Inhibition of Receptor Binding by High-Affinity RNA Ligands to Vascular Endothelial Growth Factor", Biochem. (1994), 33(34), 10450-10456.
Jeong et al., "Superparamagnetic Colloids: Controlled Synthesis and Niche Applications", Advanced Materials, vol. 19, pp. 33-60 (2007).
Jin et al., "Giant Coercive Field of Nanometer-Sized Iron Oxide", Advanced Materials, vol. 1, No. 1, pp. 48-51 (2004).
Kaner et al., "Fibroblast Growth Factor Receptor Is a Portal of Cellular Entry for Herpes Simplex Virus Type 1", Science (1990), 248, 1410-1413.
Kimball, http://users.rcn.com/jkimball.ma.ultranet/BiologyPages/D/Diffusion.html, Cached Feb. 2003 (wayback machine), 10 pages.
Kjeldsen, "Preparation and Characterization of Monoclonal Antibodies Directed to the Tumor-associated O-linked Sailosyl-2-6 a-N-Acetylgalactosaminyl (Sialosyl-Tn) Epitope", Cancer Research (1988), 48, 2214-2220.
Klatzmann et al., "T-lymphocyte T4 molecule behaves as the receptor for human retrovirus LAV", Nature (1984), 312, 767-768.
Krah et al., "Characterization of Octyl Glucoside-Solubilized Cell Membrane Receptors for Binding Measles Virus", Virology (1989), 172, 386-390.
Kresge et al., "Ordered Mesoporous Molecular Sieves Synthesized by a Liquid-Crystal Template Mechanism", Nature 359:710 (1992).
Lai et al., "Functional Polymers from Novel Carboxyl-Terminated Trithiocarbonates as Highly Effecient RAFT Agents", Macromolecules, vol. 35, pp. 6754-6756 (2002).
Lan et al., "Isolation and Properties of a Human Pancreatic Adenocarcinoma-associated Antigen, DU-PAN-2", Cancer Res. (1985), 45, 305-310.
Lemaire et al., "Interaction of Membrane Proteins and Lipids with Solubilizing Detergents", Biochim. et Biophys. Acta 1508:86-111 (2000).
Lentz et al., "Is the Acetylcholine Receptor a Rabies Virus Receptor?", Science (1982), 215, 182-184.
Li et al., Pharmaceutical Research, v. 24, No. 3, 2007 (pub. online Jan. 25, 2007).
Liang, "Artificial 'Cells' as Advanced Delivery Vesicles", Department of Metallurgical and Materials Engineering, Colorado School of Mines (2008).
Liang et al., "Inherently Tunable Electrostatic Assembly of Membrane Proteins", Nano. Lett. 8:333-339 (2008).
Liang et al., "The Directed Cooperative Assembly of Proteorhodopsin into 2D and 3D Polarized Arrays", Proc. Natl. Acad. Sci. U.S.A. 204:8212-8217 (2007).
Lin et al., "Well-Ordered Mesoporous Silica Nanoparticles as Cell Markers", Chem. Mater. 17:4570 (2005).
Lu et al., "Aerosol-Assisted Self-Assembly of Mesostructured Spherical Nanoparticles", Nature 398:223 (1999).
Lu et al., "Mesoporous Silica Nanoparticles as a Delivery System for Hydrophobic Anticancer Drugs", Small (2007), 3(8), 1341-1346.
Lysenko et al., "Solution behavior and self-assembly of complexes from poly(alph-methylstyrene)-block-poly(N0ethyl-4-vinylpyridinium) cations and aerosol OT anions", Macromolecules, 1998, 31:4516-4519.
Marlin et al., "A soluble form of intercellular adhesion molecule-1 inhibits rhinovirus infection", Nature (1990), 344, 70-72.
Mendelsohn, "Cellular Receptor for Poliovirus: Molecular Cloning, Nucleotide Sequence, and Expression of a New Member of the Immunoglobulin Superfamily", Cell (1989), 56, 855-865.
Mornet et al., "The Formation of Supported Lipid Bilayers on Silica Nanoparticles Revealed by Cyroelectron Microscopy", Nano Lett. 5(2):281-285 (2005).
Napier et al., Polym. Rev., 2007, v. 47, p. 321.
Nooney et al., "Synthesis of Nanoscale Mesoporous Silica Spheres with Controlled Particle Size", Chem. Mater. 14:4721 (2002).

(56) References Cited

OTHER PUBLICATIONS

Park et al., "Controlled Release of Guest Molecules from Mesoporous Silica Particles Based on a pH-Responsive Polypseudorotaxane Motif", Angew. Chem. Intl. Ed. 46:1455-1457 (2007).
Park, "Tumor-directed Targeting of Liposomes", Biosci. Rep. (2002), 22(2), 267-281.
Phoochinda et al., "An Algal Removal Using a Combination of Flocculation and Flotation Processes", Environmental Technology, 25:12, pp. 1385-1395 (2004).
Remington, "Remington: Practice of The Science and Pharmacy", 19th Edition, Alfonso R. Gennaro, ed., (1995) Chapter 83, 1447-1675.
Rigaud et al., "Reconstitution of Membrane Proteins into Liposomes", Methods Enzymol. 372:65-86 (2003).
Ruff et al., "CD4 receptor binding peptides that block HIV infectivity cause human monocyte chemotaxis", FEBS Letters (1987), 211(1), 17-22.
Ryoo et al., "Ordered Mesoporous Carbons", Adv. Mater. 13:677 (2001).
Sacerdote et al., "Vasoactive Intestinal Peptide 1-12: A Ligand for the CD4 (T4)/Human Immunodeficiency Virus Receptor", J. Neuroscience Research (1987), 18, 102-107.
Schuerch et al., "Molecular Basis of Listeriolysis Oph Defendence", Proc. Natl. Acad. Sci. U.S.A. 102:12537-42 (2005).
Shepley et al., "Monoclonal antibody identification of a 100-kDa membrane protein in HeLa cells and human spinal cord involved in poliovirus attachment", Proc. Nat'l. Acad. Sci. U.S.A. (1988), 85, 7743-7747.
Shi et al., "Porous Carbon and Carbon/Metal Oxide Mircrofibers with Well-Controlled Pore Structure and Interface", Journal of the American Chemical Society, vol. 130, pp. 5034-5035 (2008).
Slowing et al., "Mesoporous Silica Nanoparticles for Intracellular Delivery of Membrane-Impermeable Proteins", J. Am. Chem. Soc. (2007), 129, 8845-8849.
Smith et al., "Endocytosis at the Blood-Brain Barrier: From Basic Understanding to Drug Delivery Strategies", J. Drug Target 14:191 (May 2006).
Solberg et al., "Adsorption of DNA into Mesoporous Silica", J. Phys. Chem. B. (2006), 110(31), 15261-15268.
Springer et al., "Blood Group Tn-Active Macromolecules from Human Carcinomas and Erythrocytes: Characterization of and Specific Reactivity with Mono- and Poly-Clonal Anti-Tn Antibodies Induced by Various Immunogens", Carbohydr. Res. (1988), 178, 271-292.
Stein et al., "Hybrid Inorganic-Organic Mesoporous Silicates—Nanoscopic Reactors Coming of Age", Adv. Mater. 12:1403 (2000).
Sudimack et al., "Targeted Drug Delivery Via the Folate Receptor", Adv. Drug Deliv. Rev. 41:147-162 (2000).
Tian et al., "Self-Adjusted Synthesis of Ordered Stable Mesoporous Minerals by Acid-Base Pairs", Nat. Mater. 2:159 (2003).
Tjandra, et al., "Application of mammary serum antigen assay in the management of breast cancer: a preliminary report", Br. J. Surg. (1988), 75(8), 811-817.
Tohver et al., "Nanoparticle halos: A New Colloid Stabilization Mechanism", University of Illinois at Urbana-Champaign, Urbana, IL, www.pnas.org/cgi/doi/10.1073/pnas.151063098, 5 pages, 2001.
Tomlinson et al., "Methods for Generating Multivalent and Bispecific Antibody Fragments", Methods in Enzymology (2000), 326, 461-479.
Trewyn et al., "Synthesis and Functionalization of a Mesoporous Silica Nanoparticle Based on the Sol-Gel Process and Applications in Controlled Release", Adv. Funct. Mater. 17:1225-1236 (2007).
Tuerk et al., "In vitro evolution of functional nucleic acids: high-affinity RNA ligands of HIV-1 proteins", Gene. (1993), 137, 33-39.
Uhrich et al., "Polymeric Systems for Controlled Drug Release", Chem. Rev. 99:3181 (1999).
Vallet-Regi et al., "Mesoporous Materials for Drug Delivery", Angew. Chem. Int. Ed. 46:7548-7558 (2007).
Wang et al., "A Molecularly Imprinted Polymer-Coated Nanocomposite of Magnetic Nanoparticles for Estrone Recognition", Talanta, vol. 78, pp. 327-332 (2009).
Wang et al., "Mesenchymal stem cell intracellular labeling using silica-coated superparamagnetic iron oxide nanoparticles with amine functional peripheries", IEEE, 2008, 187-189.
Ward et al., "Binding activities of a repertoire of single immunoglobulin variable domains secreted from *Escherichia coli*", Nature (Oct. 12, 1989), 341, 544-546.
Weis et al., "Structure of the influenza virus haemagglutinin complexed with its receptor, sialic acid", Nature (1988), 333, 426-431.
White et al., "Viral Receptors of the Immunoglobulin Superfamily", Cell (1989), 56, 725-728.
Wyrick et al., "Entry of Genital Chlamydia trachomatis into Polarized Human Epithelial Cells", Infect. and Immunity (1989), 57(8), 2378-2389.
Yi et al., "Silica-Coated Nanocomposites of Magnetic Nanoparticles and Quantum Dots", Journal of American Chemical Society, vol. 127, pp. 4990-4991 (2005).
Yiu et al., "A triple-layer design for polyethyleneimine-coated, nanostructured magnetic particles and their use in DNA binding and transfection", Nanotechnology, 2007, 18:1-6.
Zhang et al., "Thermo and pH Dual-Responsive Nanoparticles for Anti-Cancer Drug Delivery", Adv. Mater. 19:2988 (2007).
Zhao et al., "Triblock Copolymer Synthesis of Mesoporous Silica with Periodic 50 to 300 Angstrom Pores", Science 279:548 (1998).
Zola, "Monoclonal Antibodies: Preparation and Use of Monoclonal Antibodies and Engineered Antibody Derivatives, Pring Verlag (Dec. 15, 2000; 1st edition)".

\* cited by examiner

HARVESTING MICRO ALGAE

CROSS REFERENCE TO RELATED APPLICATIONS

The present application is a divisional application of U.S. patent application Ser. No. 13/011,582, filed Jan. 21, 2011, now abandoned, which claims the benefit of priority under 35 U.S.C. §119(e) to U.S. provisional application 61/297, 533 filed Jan. 22, 2010, the contents of which are hereby incorporated by reference in their entirety. The present application is related to U.S. provisional application Ser. No. 12/704,416, filed Feb. 11, 2010, titled NANOPARTICLES, COMPOSITIONS THEREOF, AND METHODS OF USE, AND METHODS OF MAKING THE SAME.

BACKGROUND

The subject technology relates generally to devices and methods for isolating microorganisms.

Microorganisms have many commercial applications. Bacteria, fungi, and algae may be used in various applications for the production of pharmaceuticals, food, supplements, and even fuel. For example, algae have applications in pharmaceutical, food, and biofuel production.

Microalgae is a term that may be used to distinguish single-celled, generally microscopic algae from multicellular algae. Algae may be found in fresh as well as salt water environments.

Use of microalgae in commercial applications may depend in part on understanding the biochemical and genetic makeup of microalgae. In addition, commercial application may also require cost-effective methods for handling microalgae. For example, at present microalgae harvesting techniques may limit their successful commercialization in the production of microalgae-based biofuels.

Some characteristics of microalgae may present challenges for their efficient harvest. For example, microalgae are generally small (a few to a few hundred micrometers), with low specific gravity, and a generally negative overall surface charge. In addition, microalgae may grow at low cell densities in water.

Current techniques used in harvesting microalgae may include centrifugation, filtration, flotation, flocculation, and ultrasound sedimentation etc. Each of the present harvesting techniques may have limitations. For example, centrifugation and ultrasound sedimentation may be slow processes with concomitantly high operation costs; filtration may be subject to clogging and shortened run times; flotation may require use of surfactants that may hamper downstream processes; and flocculation may require various chemical additives such as pro-oxidants (to induce liberation of extracellular organic matter), electrolytes (e.g. chitosan), or Al- and Fe-based compounds (to neutralize the surface charge and aid cell-to-cell adhesion). In addition, some of these techniques must be combined for efficient microalgae processing, for example flocculation may also require centrifugation in order to collect slowly-settled microalgae. Chemicals used in some of these (such as flocculation or flotation) may inhibit microalgae growth and may be detrimental for continuous growth-harvest cycled operation.

In some cases, microalgae flocculation has been modeled using theories of colloidal stability. For example, the use of polyelectrolyte-induced flocculation for microalgae harvesting can be understood by DLVO theory of colloidal stability (DLVO stands for Derjaguin, Landau, Verwey and Overbeek who made seminar contribution to the theory. See: R J Hunter, *Foundations of Colloid Science*, Clarendon Press, Oxford). DLVO theory models flocculation in terms of the interplay between electronic double layer repulsion, van der Waals attraction and entropic depletion interactions.

What is needed is an efficient method of harvesting microorganisms like microalgae, that has little or no adverse impact on downstream processes, and that is low-cost.

SUMMARY

The present disclosure is directed to composite particles comprising a paramagnetic core, the core being encased in a coating of a protective material, and the coating grafted to long, polymeric chains designed to interact with a microorganism.

In various embodiments of the present composite particle the paramagnetic core may comprise iron-oxide, the protective material coating may comprise silica, and the polymeric chains may be hydrophilic and/or carry a net charge in aqueous solution.

The size of the paramagnetic core may be between about 1 nanometer to about 10 micrometers, and may have a protective coating from about 10 nm to about 10 micrometers. The polymeric chains may be generally from about 0.1 to about 100 µm (micrometers) in length with a molecular mass up to about $10^7$ Daltons (Da).

Methods for using the composite particle are also disclosed. In some embodiments, the particle may be used in harvesting microorganisms from a liquid medium comprising the use of an externally applied magnetic field. In various embodiments the particle may be used in a method of harvesting microalgae used in biofuel production. In various other embodiments the particle may be used in a method of harvesting microalgae in water treatment. In various other embodiments the particles may be used in a method of destabilizing colloidal mixtures.

The currently disclosed composite particle may be mass-produced at low cost and in some embodiments the particle is capable of re-use. In some embodiments the present method may require little or no post-harvest processing in order to remove chemicals, reagents, or materials. In various other embodiments, the method may involve a de-watering step which may require little maintenance, result in high concentration factors, consume little energy, and be operated continuously. Finally in many embodiments the currently claimed method may have little or no adverse effect on downstream processes.

DETAILED DESCRIPTION

The present disclosure is directed to composite particles comprising a paramagnetic core, the paramagnetic core being encased in a coating of a protective material, and the coating grafted to long, polymeric chains designed to interact with a microorganism.

In various embodiments of the present composite particle, the paramagnetic core may comprise iron-oxide, the protective coating may comprise silica, and the polymeric chains may be hydrophilic and/or carry a net charge in water.

The size of the paramagnetic core may vary from about 1 nanometer to about 10 micrometers. The thickness of the protective coating may be from about 10 nm to about 10 micrometers. The polymeric chains may be generally 0.1 to 100 micrometers in length with a molecular mass from about $10^1$ to about $10^7$ Daltons (Da).

Methods for using the composite particle as coagulation devices are also disclosed. In some embodiments, the particles may be used in harvesting microorganisms from a liquid medium involving the use of an externally applied magnetic field. In various embodiments the particle may be used in a method of harvesting microalgae used in biofuel production. In various other embodiments the particle may be used in a method of harvesting microalgae in water treatment. In various other embodiments the particle may be used in a method of destabilizing colloidal mixtures.

The currently disclosed composite particle may be mass-produced at low cost and in some embodiments the particle is capable of re-use. In some embodiments the present method may require little or no post-harvest processing to remove chemicals, reagents, or materials. In various other embodiments, the method may involve a de-watering step which may be of low maintenance, result in high concentration factors, consume little energy, and be operated continuously. Finally in many embodiments the currently claimed method may have little or no adverse effect on downstream processes.

Figure 1:
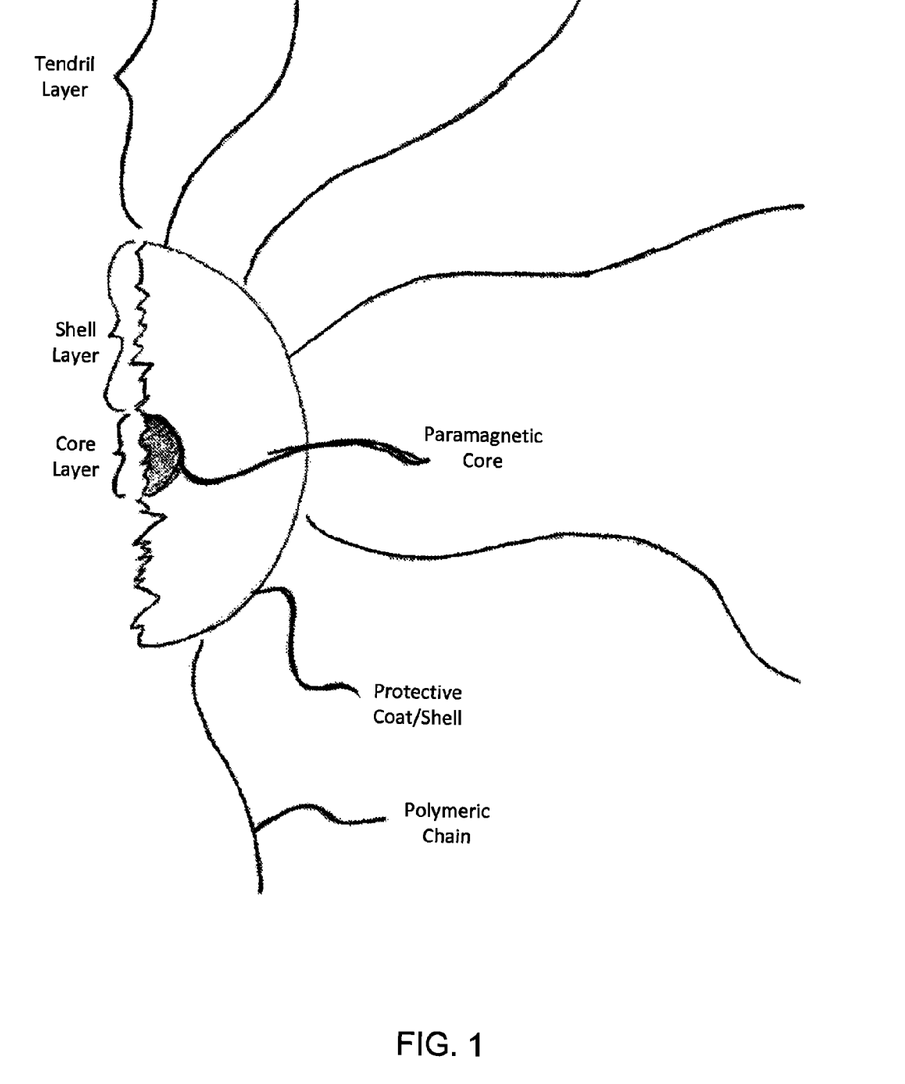
FIG. 1 is a diagram of an embodiment of the presently disclosed composite paramagnetic particle.

As depicted in FIG. 1, the presently disclosed composite paramagnetic particle may comprise three general layers: (1) a core; (2) a protective coat or shell which encases the core; and (3) a tendril layer comprising polymer chains grafted on, to, or from the protective coating.

In various embodiments the paramagnetic core may comprise a $\gamma$-$Fe_2O_3$. The iron oxide allows the core to exhibit magnetism in response to an externally applied magnetic field, while exhibiting little or no magnetism in the absence of an external magnetic field. In various embodiments the core may comprise $Fe_3O_4$. In other embodiments the core may comprise other paramagnetic particles comprising, for example, Co, CoPt, CoO, $CoFe_2O_4$, Fe, FePt, Ni etc.

The protective shell may help prevent leaching of the paramagnetic material out of the core as well as create a surface for attachment or grafting of polymeric chains. The protective coating may also aid in imparting wettability to the particle.

In various embodiments the protective coating material may be silica. A silica shell may help provide a rich chemistry (silane chemistry) for modifying the surface of the particle.

The tendril layer may aid in interacting with microorganisms. The tendril layer may also help improve the dispersion of composite particles. The polymeric chains of the tendril layer may help promote aggregation of microorganisms. The polymeric chains may be designed to interact with microorganisms in various ways, for example through electrostatic interactions, van der Waals forces, and entropic depletion effects. In further embodiments the interactions may involve a combination of various forces.

In various embodiments, composite paramagnetic particles may be added to a solution containing a microorganism. The polymeric chains of the particles may interact with microorganisms within the solution. A composite paramagnetic particle may have multiple polymeric chains which may allow an individual particle to aggregate several microorganisms. After allowing the composite particles and microorganisms to interact, an external magnetic field may be applied. The application of an external magnetic field may result in attracting the paramagnetic core to the magnetic source. This attraction may result in concentration and/or precipitation of the microorganism.

The presently disclosed composite particles may be used to rapidly precipitate microorganisms from various solutions. In some embodiments the microorganism solution may be less than 10 liters. In other embodiments the microorganism solution may be greater than 10 liters. In some embodiments the composite particle may be used to continuously harvest microorganisms.

The presently disclosed composite particles may cause little or no adverse interference to common processing steps performed on microorganisms. For example, the disclosed composite particle may be used in lipid extraction methods, solvent extraction, mechanical press, and/or supercritical water extraction. Additionally, the particle may be used to recover microorganisms from solution without additional mechanical or chemical processing. After elution of the microorganism from the composite particle, the composite particle may be re-collected by magnetic force and re-used.

The choice of particle sizes, volume fractions, polymer chain length, compositions and charge states may be varied to optimize efficient harvesting of various target microorganisms.

Paramagnetic Core

Paramagnetic refers to substances that may exhibit magnetism in response to an external magnetic force. Paramagnetic substances generally do not exhibit magnetism in the absence of an externally applied magnetic force.

A wide variety of methods have been reported for making paramagnetic particles. For instance, paramagnetic $\gamma$-$Fe_2O_3$ particles can be prepared by injecting $Fe(CO)_5$ into a hot surfactant mixture of octyl ether and oleic acid (see descriptions in: Hyeon T et al, *J. Am. Chem. Soc.*, 2001, 123, 12798-12801), and paramagnetic $Fe_3O_4$ particles can be prepared by an autoclave reaction of $FeCl_3$, ethylene glycol, NaAc, and polyethylene glycol mixture solution (see descriptions in: Deng H et al, *Angew. Chem. Int. Ed.* 2005, 44, 2782-2785). Preparation of other paramagnetic particles are also well documented (see for example: Jeong U et al, *Adv. Mater.* 2007, 19, 33-60 and references therein).

The composite particle may comprise a generally paramagnetic core. Various materials may be used to construct the paramagnetic core of the composite particle device. In some embodiments, the core material may comprise iron oxide. The magnetic core may also comprise other metal oxides such as Co. In further embodiments, the magnetic core may also include non-metal oxide materials like Co, CoPt, Fe, FePt, Ni etc. may be used. Further, those skilled in the art will recognize that different materials may be combined in the manufacture of these particles.

The paramagnetic core as described herein is generally between about 1 nanometer and about 10 micrometers in size. The paramagnetic core may have various shapes, including rods, spheres, and platelets.

In various embodiments, the paramagnetic core may measure greater than 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, or 240 nm in at least one measureable dimension. In other embodiments, particles may measure less than 250 nm, 240 nm, 230 nm, 220 nm, 210 nm, 200 nm, 190 nm, 180 nm, 170 nm, 160 nm, 150 nm, 140 nm, 130 nm, 120 nm, 110 nm, 100 nm, 90 nm, 80 nm, 70 nm, 60 nm, 50 nm, or 40 nm in at least one measurable dimension.

Protective Coating of Paramagnetic Core

In various embodiments, the paramagnetic core may be coated with a protective material. The protective material may help to encase the paramagnetic material of the core and may also provide a surface for attachment and/or grafting of polymeric chains.

The protective material may create a shell of variable thickness. In some embodiments, the shell may be about 100 nm. In other embodiments the protective shell may be generally less than 100 nm thick. In other embodiments the shell may be generally greater than 100 nm thick.

In various embodiments the material used to coat the paramagnetic cores comprises silica. Silanization of the particle may help create a functional coating for grafting or attaching polymer chains to the nanoparticle. Alternative embodiments may use non-silica materials, including but not limited to polymeric film, carbon, carbon nitride, boron nitride etc.

In various embodiments, silanization may include preparing a functional silane solution using anhydrous solvents and adding paramagnetic core material to the silane solution, followed by allowing the solution to react then washing and drying the particles. In other embodiments, silanization may include the use of reverse microemulsion where the paramagnetic cores are dispersed in a water-in-surfactant reverse microemulsion, and hydrolyzation of alkyl silane leads to the formation of silica coating around the paramagnetic core (see for example: Yi D K et al, *Chem. Mater.*, 2006, 18, 614-619). In some embodiments the functional silanes may have a generic form of $R^1_x$—Si—$(OR^2)_{4-x}$, where x is 1, 2, or 3, $R^2$ is usually an alkyl-group, $R^1$ is an alkyl chain with a functional moiety as the end group. In some embodiments the functional moiety may be alkyl, alkene, alkyne, aryl, azide, hydroxyl, carboxyl, amine, amino, thio, epoxy, cyano, or halogen.

The protective coating may be modified prior to the graft-to or graft-from polymerization methods to aid in covalently bonding a variety of polymers with controllable chain length to the coating. For example, a silica coat may be modified, for instance, by (3-Aminopropyl)triethoxysilane or 5,6-Epoxyhexyltriethoxysilane, and anchored with RAFT (reversible addition-fragmentation chain transfer) functionalities. This modification may allow for "controlled/living polymerization" of grafted polymers (an example is as described in "Functional polymers from novel carboxyl-terminated trithiocarbonates as highly efficient RAFT agents" by Lai, J. T.; Filla, D.; Shea, R., *Macromolecules* 2002, 35, 6754-6756). Controlled/living polymerization describes polymerization in which termination of a growing polymer chain is inhibited, and the polymer chain may grow until monomers are consumed after which polymerization may again continue if new monomers are added to the reaction. RAFT is one example of controlled/living polymerization.

Polymeric Chain

In various embodiments, the outmost layer of the disclosed composite particles is comprised of grafted polymer chains. The polymeric chain length may be varied to aid in interacting with a target microorganism. In various embodiments the polymeric chains may vary from about 0.1 μm and about 100 μm. In various embodiments the polymeric chains may be less than 0.1 μm in length. In various embodiments the polymer chain length may be greater than 100 μm.

Polymeric chains may vary in molecular mass from about 1 kDa to about 10,000 kDa. In various embodiments the polymeric chains may be less than 1 kDa. In various embodiments the polymeric chains may be greater than 10,000 kDa.

In various embodiments the polymers are comprised of subunits that are hydrophilic. In some embodiments the polymer chain may be comprised of subunits that are generally negatively charged. In other embodiments the polymer chain may be comprised of subunits that are generally positively charged. In various other embodiments the polymeric subunits comprising the polymer chain may be neutral, negatively charged, and/or positively charged. In other embodiments the polymeric subunits may be chosen to select a generally uniform or non-uniformly charged polymer chain. In various embodiments the polymer chain may be neutral.

In various embodiments the number of polymeric chains per composite paramagnetic particle is between about 5 and about 20 chains. In various embodiments individual particles may have less than about 5 chains. In various other embodiments individual nanoparticles may have more than 20 polymeric chains.

The polymeric chains may be generally flexible to aid in interacting with target microorganisms.

In various embodiments the polymer chain may be generally cationic. In those embodiments the polymers include, but are not limited to, chitosan, poly (N-ethyl-4-vinypyridinium), poly(2,2-(dimethyl aminoethyl methacrylate), poly (ethylene imine), poly(allylamine), and poly(diallyl dimethyl ammonium chloride) etc.; In various embodiments the polymer chain may be generally anionic. In those embodiments the polymers include, but are not limited to, poly (acrylic acid), poly(styrene sulfonate), poly(vinyl sulfate), and poly(3-sulfopropyl methacrylate) etc.; In various other embodiments the polymer chain may be generally hydrophilic and neutral. In those embodiments the polymers include, but are not limited to, polyethylene glycol, poly(2-methyloxazoline, poly(2-ethyl-2-oxazoline), and polyacrylic amide etc.

The polymeric chains may be generally homogeneous on an individual composite particle, that is all chains on a composite paramagnetic particle may be substantially similar in length, weight, composition, charge, etc. In various other embodiments the polymeric chains on an individual composite particle may vary, that is, various chains on an individual particle may differ in length, mass, composition, and/or charge etc.

Various methods are available to elute microorganisms from the composite paramagnetic particles after recovery of the microorganism. For example, elution may be achieved by treating the composite particle-bound microorganism with a high or low ionic strength solution, organic solvent and/or ionic liquid extraction, and/or supercritical water treatment etc.

Polymerization

In various embodiments the grafted polymer chains are formed by step-growth or chain-growth polymerization. Step growth may be referred to polymerization that occurs in a stepwise fashion, for example monomer→dimer→trimer→etc. This type of polymerization may involve reaction of functional groups between monomers (such as —OH and —COOH) and as a result, the molar mass increases slowly. Chain grown may refer to a fast linkage of monomers by initiation (activate the unsaturated bonds). During chain growth, the molar mass may increase rapidly. In some embodiments the polymerization process occurs as controlled/living polymerization, such as for example RAFT polymerization. Controlled/living polymerization describes polymerization in which termination of a growing polymer chain is inhibited, and the polymer chain may grow until monomers are consumed after which polymerization again continue if new monomers are added to the reaction. RAFT is one example of living polymerization.

RAFT polymerization operates on the principle of degenerative chain transfer (see review: Moad G et al, *Aust. J. Chem.*, 2005, 58, 379-410). Without being limited to a particular mechanism, Scheme 1 shows a proposed mechanism for RAFT polymerization. In Scheme 1, RAFT polymerization involves a single- or multi-functional chain transfer agent (CTA), such as the compound of formula (I), including dithioesters, trithiocarbonates, xanthates, and dithiocarbamates. The initiator produces a free radical, which subsequently reacts with a polymerizable monomer. The monomer radical reacts with other monomers and propagates to form a chain, Pn*, which can react with the CTA. The CTA can fragment, either forming R*, which will react with another monomer that will form a new chain Pm* or Pn*, which will continue to propagate. In theory, propagation to the Pm* and Pn* will continue until no monomer is left or a termination step occurs. After the first polymerization has finished, in particular circumstances, a second monomer can be added to the system to form a block copolymer.

In particular embodiments, RAFT polymerization is used to produce a variety of well-defined, novel biopolymers as constructs for multifunctional systems for the surface modification of disclosed composite particles consisting of a paramegnetic core encased in a protective coating. The inherent flexibility of RAFT polymerizations makes it a candidate to produce well-defined polymer structures.

In various embodiments, the polymerization process is Atom Transfer Radical Polymerization ("ATRP") ATRP is an example of controlled/living radical polymerization. In some embodiments, ATRP employs atom transfer from an organic halide to transition-metal complex to generate the reacting radicals, followed by back transfer from the transition metal to a product radical to form the final polymer product. One example of ATRP may be found in, Patten T E, Matyjaszewski K, "Atom Transfer Radical Polymerization and the Synthesis of Polymeric Materials", which is incorporated herein in its entirety. (*Adv. Mater.*, 1998, 10, 901-915).

In various embodiments, the polymerization process is ring-opening polymerization. Ring-opening polymerization is a form of chain-growth polymerization, in which the terminal end of a polymer acts as a reactive center, where further cyclic monomers join to form a larger polymer chain through ionic propagation. One example of ring-opening polymerization may be found in, Dechy-Cabaret O et al, "Controlled ring-opening polymerization of lactide and glycolide", which is incorporated herein in its entirety. (*Chem. Rev.*, 2004, 104, 6147-6176).

Scheme 1

RAFT polymerization involves a similar mechanism as traditional free radical polymerization systems, with the difference of a purposely added CTA. Addition of a growing chain to a macro-CTA yields an intermediate radical, which can fragment to either the initial reactants or a new active chain. With a high chain transfer constant and the addition of a high concentration of CTA relative to conventional initiator, synthesis of polymer with a high degree of chain-end functionality and with well defined molecular weight properties is obtained.

RAFT polymerization may be used in the synthesis of multifunctional polymers due to the versatility of monomer selection and polymerization conditions, along with the ability to produce well-defined, narrow polydispersity polymers with both simple and complex architectures.

In various embodiments, the polymerization process is anionic polymerization. Anionic polymerization is a form of chain-growth polymerization that involves the polymerization of vinyl monomers with strong electronegative groups. One example of anionic polymerization may be found in Hsieh H and Quirk R "Anionic Polymerization: Principles and practical applications", which is incorporated by reference in its entirety. (Marcel Dekker, Inc: New York, 1996);

In various embodiments, the polymerization process is cationic polymerization. Cationic polymerization is a type of chain growth polymerization in which a cationic initiator molecule binds and transfers charge to a monomeric unit, which becomes reactive as a result and reacts similarly with other monomeric units to form a polymer. One example of cationic polymerization may be found in Odian G, "Principles of Polymerization", which is incorporated by reference in its entirety. (Wiley-Interscience, Hoboken, N.J., 2004)

In certain aspects, pre-formed polymers may be grafted to the protective coating instead of the graft-from polymerization on the protective coating.

Flocculation

Inter-particle forces, as well as hydrodynamics, and solution conditions (pH, ion strength, etc.) may aid in the harvesting of microalgae from solutions. For example, DLVO flocculation theory posits that identifiable distances may exist (primary and secondary minima) at which the forces of attraction may exceed those of electrostatic repulsion which may result in adhesion. DLVO theory may be used to model the present interaction between microalgae and the currently disclosed composite particle device.

Some studies in colloidal science have recently revealed that extremely low nanoparticle volume fractions ($<10^{-5}$) could be used to stabilize or flocculate colloidal suspensions depending on the nature of colloid-nanoparticle interactions (see: Tohver, V. et al, *Proc. Natl. Acad. Sci. U.S.A.*, 2001, 98, 8950-8954).

In various embodiments the composite particles may be added to a solution containing microorganisms and allowed to interact. In various embodiments the solution may be stirred to help facilitate interaction between the composite particles and microorganisms.

EXAMPLES

Example 1

Figure 3A:
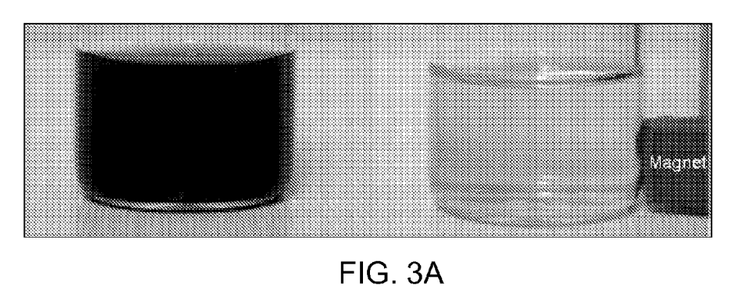
FIG. 3A depicts rapid precipitation of the present composite paramagnetic $Fe_2O_3$ particle device by introduction of an external magnetic field.
Figure 3B:
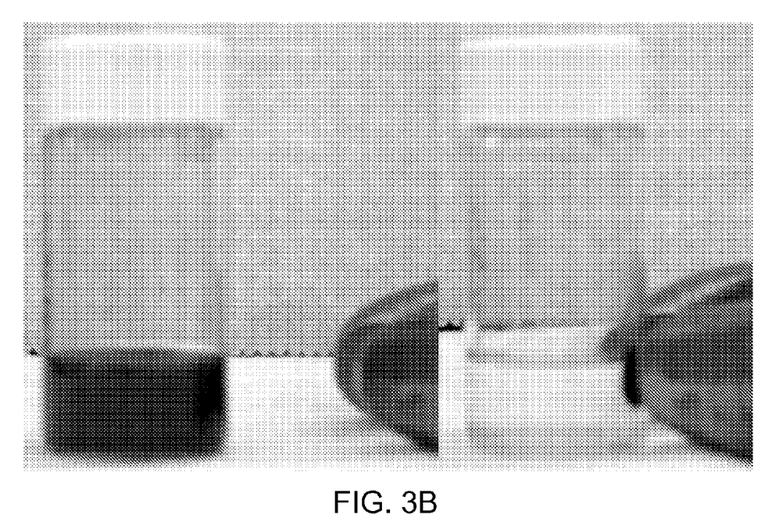
FIG. 3B depicts rapid precipitation of the present composite paramagnetic $Fe_3O_4$ particle device by introduction of an external magnetic field.

The presently disclosed $\gamma$-$Fe_2O_3$@$SiO_2$ composite particles may be well dispersed in solution. FIG. 3A, at left shows a solution of silica coated Fe-oxide nanoparticles in solution. The photo at right in FIG. 3A shows the solution shortly after introduction of an external magnetic field. This figure demonstrates that a homogeneous solution of the present composite particle devices may be rapidly, efficiently, and inexpensively concentrated. The presently disclosed composite particles can be precipitated out of solution rapidly under magnetic field (FIG. 3A). FIG. 3B depicts similar results using $Fe_3O_4$ particles.

Example 2

Figure 2:
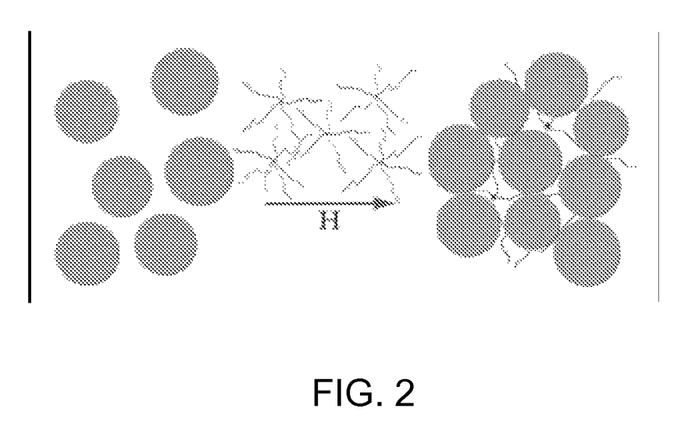
FIG. 2 depicts the presently disclosed composite paramagnetic particles with grafted polymers adhering to microalgae.

The presently disclosed $\gamma$-$Fe_2O_3$@$SiO_2$@Polymer composite particles are used as coagulation agents to rapidly and efficiently concentrate microalgae from growth medium under external magnetic field (H), as schematically depicted in FIG. 2. The composite particles are able to be re-used after microalgae elution or biofuel extraction, thus greatly reduce the cost.

Example 3

Figure 4:
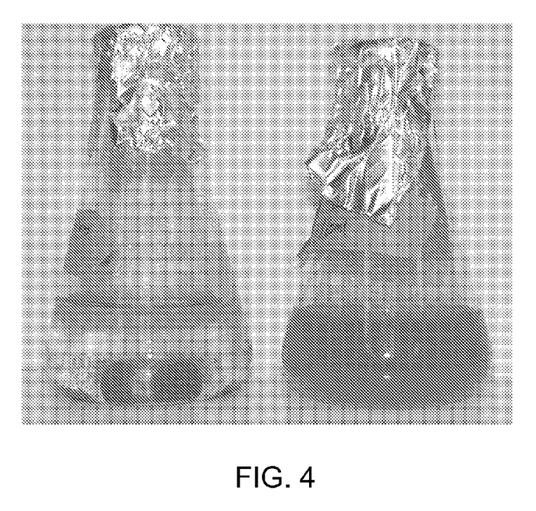
FIG. 4 depicts rapid coagulation of microalgae from a rich algal growth medium by applying a minuscule amount of the present composite paramagnetic particles (a few milligrams) and a moderate external magnetic field (provided by a magnetic stirrer bar).

$Fe_3O_4$@$SiO_2$@Polymer composite particles were used as coagulation agents to rapidly and efficiently concentrate microalgae from a rich algal growth medium. A moderate external magnetic field (H) was provided by a magnetic stirrer bar. The microalgal strain used was *Nannochloropsis*, which has a small diameter (~2 μm) and low specific density due to high oil content (~50% by dry weight). *Nannochloropsis* is extremely hard to harvest via conventional methods. FIG. 4 shows nearly 100% coagulation of *Nannochloropsis* occurs in a few seconds after adding a few milligrams of the presently disclosed $Fe_3O_4$@$SiO_2$@Polymer composite particles (right: before coagulation; left: after coagulation).

All directional references (e.g., upper, lower, upward, downward, left, right, leftward, rightward, top, bottom, above, below, inner, outer, vertical, horizontal, clockwise, and counterclockwise) are only used for identification purposes to aid the reader's understanding of the example of the invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected with another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

It will be apparent to those of ordinary skill in the art that variations and alternative embodiments may be made given the foregoing description. Such variations and alternative embodiments are accordingly considered within the scope of the present invention.

What is claimed is:

1. A method of using a composite particle to recover a microorganism from a solution comprising:
   adding at least one composite particle to a solution comprising microorganisms, wherein the composite particle has a paramagnetic core, a silica shell coating the core, and a plurality of polymeric chains having a molecular mass of 1 to 10,000 kDa grafted onto the silica shell;
   allowing the composite particles and microorganisms to interact in the solution such that one or more microorganisms aggregate with a composite particle;
   applying an external magnetic field to the solution; and
   recovering the composite particle-microorganism aggregates from the solution.

2. The method of claim 1, wherein the polymeric chains interact with the microorganisms to promote aggregation of the microorganisms.

3. The method of claim 1, wherein the microorganism is microalgae.

4. The method of claim 3, wherein the microalgae is *Nannochloropsis*.

5. The method of claim 3, wherein the microalgae are producing biofuels.

6. The method of claim 1, wherein the solution is drinking water.

7. The method of claim 1, further comprising allowing the composite particles to be suspended in the solution after addition of the particles to the solution.

8. The method of claim 7, further comprising collecting and reusing the composite particles after elution of the microorganism from the composite particle.

9. The method of claim 1, further comprising eluting the microorganisms from the composite particle-microorganism aggregates.

10. The method of claim 1, wherein the paramagnetic core comprises iron oxide.

11. The method of claim 1, wherein the paramagnetic core comprises $Fe_2O_3$.

12. The method of claim 1, wherein the paramagnetic core comprises $Fe_3O_4$.

13. The method of claim 1, wherein the polymeric chains are hydrophilic.

14. The method of claim 1, wherein the polymeric chains have a net positive charge.

15. The method of claim 1, wherein the polymeric chains have a net negative charge.

16. The method of claim 1, wherein the polymeric chains have no net charge.

17. The method of claim 1, further comprising first producing the composite particle by grafting the polymeric chains onto the silica shell by one or more of step-growth polymerization, chain-growth polymerization, and controlled/living polymerization.

18. The method of claim 17, wherein grafting by controlled/living polymerization is one or more of reversible addition fragmentation transfer polymerization, atom transfer radical polymerization, ring-opening polymerization, anionic polymerization, and cationic polymerization.

19. The method of claim 18, wherein grafting is by reversible addition fragmentation transfer polymerization.

20. The method of claim 18, further comprising modifying the silica coating by 3-aminopropyl-triethoxysilane or 5,6-epoxyhexyltriethoxysilane prior to grafting the polymeric chains.

* * * * *